(12) United States Patent
Gray

(10) Patent No.: US 9,550,015 B2
(45) Date of Patent: Jan. 24, 2017

(54) FUNCTIONALLY-CLOSED, STERILE BLOOD PROCESSING SOLUTION SYSTEM AND METHOD

(71) Applicant: Biomet Biologics, LLC, Warsaw, IN (US)

(72) Inventor: Alan Gray, North Reading, MA (US)

(73) Assignee: Biomet Biologies, LLC, Warsaw, IN (US)

( * ) Notice: Subject to any disclaimer, the term of this patent is extended or adjusted under 35 U.S.C. 154(b) by 78 days.

(21) Appl. No.: 14/634,264

(22) Filed: Feb. 27, 2015

(65) Prior Publication Data

US 2015/0182678 A1 Jul. 2, 2015

Related U.S. Application Data

(60) Division of application No. 13/756,712, filed on Feb. 1, 2013, now Pat. No. 9,011,408, which is a (Continued)

(51) Int. Cl.
*A61M 1/02* (2006.01)
*A61J 1/14* (2006.01)
(Continued)

(52) U.S. Cl.
CPC ........... *A61M 1/0209* (2013.01); *A61J 1/1443* (2013.01); *A61M 1/02* (2013.01); *A61M 1/0218* (2014.02);
(Continued)

(58) Field of Classification Search
CPC .... A61M 1/02; A61M 1/0209; A61M 1/0218; A61M 1/0259; A61M 1/0272; A61M 1/0281; A61M 2202/0429; A61M 2205/60; A61M 2205/6009; A61M 2205/7518; A61M 39/14; A61M 39/143; A61M 39/146; A61M 2202/0413; A61M 1/3633; A61J 1/1443; B65B 1/04; Y10S 200/42; Y10S 220/29; Y10S 29/048; Y10S 604/905

See application file for complete search history.

(56) References Cited

U.S. PATENT DOCUMENTS 3,874,384 A 4/1975 Deindoerfer et al.
4,004,586 A 1/1977 Christensen et al.
(Continued)

FOREIGN PATENT DOCUMENTS

EP 0987034 A2 3/2000
WO 0113933 A2 3/2001
(Continued)

OTHER PUBLICATIONS

Brecher, M.E. et al. Rejuvenation of erythrocytes preserved with AS-1 and AS-3. A.J. Clin. Path. 96(6):767-769. 1991.
(Continued)

*Primary Examiner* — Adam Marcetich
(74) *Attorney, Agent, or Firm* — Schwegman Lundberg & Woessner, P.A.

(57) ABSTRACT

Delivering a blood processing solution to blood in a blood bag includes coupling a first tube to a vented spike at one end and to a Y-shaped tube connector at a second end. An in-line microbiotic barrier filter is coupled to the first tube between its ends. A second tube is coupled to a transfer bag at one end and to the Y-shaped tube connector at its other end. A third tube is coupled to the output of the Y-shaped tube connector and sealed at its distal end. The blood bag includes a fourth tube that is sealed at a distal end. The third tube is welded to the fourth tube using a sterile tubing welder, wherein a functionally-closed, sterile flow path through which the blood processing solution can flow into the blood bag is maintained.

20 Claims, 4 Drawing Sheets

Related U.S. Application Data continuation-in-part of application No. 13/756,116, filed on Jan. 31, 2013, now Pat. No. 9,102,918.

(51) Int. Cl.
    *B65B 1/04*         (2006.01)
    *A61M 39/14*     (2006.01)

(52) U.S. Cl.
    CPC ......... *A61M 1/0259* (2013.01); *A61M 1/0272* (2013.01); *A61M 1/0281* (2013.01); *A61M 39/14* (2013.01); *A61M 39/143* (2013.01); *A61M 39/146* (2013.01); *B65B 1/04* (2013.01); *A61M 2202/0429* (2013.01); *A61M 2205/60* (2013.01); *A61M 2205/6009* (2013.01); *A61M 2205/7518* (2013.01); *Y10S 29/048* (2013.01); *Y10S 200/42* (2013.01); *Y10S 220/29* (2013.01); *Y10S 604/905* (2013.01)

(56) References Cited

U.S. PATENT DOCUMENTS

| | | | |
|---|---|---|---|
| 4,116,646 | A | 9/1978 | Edwards |
| 4,786,286 | A | 11/1988 | Cerny et al. |
| 4,994,039 | A | 2/1991 | Mattson |
| 5,098,371 | A | 3/1992 | Juji et al. |
| 5,250,303 | A | 10/1993 | Meryman et al. |
| 6,059,968 | A * | 5/2000 | Wolf, Jr. ............. A61M 1/0209 210/252 |
| 7,723,017 | B2 | 5/2010 | Bitensky et al. |
| 2001/0036624 | A1* | 11/2001 | Sumita ................. C12N 5/0087 435/2 |
| 2001/0052497 | A1 | 12/2001 | Blickhan et al. |
| 2002/0063090 | A1 | 5/2002 | Calhoun et al. |
| 2002/0068893 | A1* | 6/2002 | Sawamoto .......... A61M 1/0218 604/6.03 |
| 2004/0015147 | A1 | 1/2004 | Mathias et al. |
| 2005/0074743 | A1 | 4/2005 | Purmal et al. |
| 2005/0233302 | A1 | 10/2005 | Hess et al. |
| 2006/0180526 | A1 | 8/2006 | Sugawara et al. |
| 2007/0043317 | A1 | 2/2007 | Sugawara |
| 2007/0095764 | A1* | 5/2007 | Yang ................... A61M 1/0218 210/767 |
| 2007/0179424 | A1 | 8/2007 | Rubinstein et al. |
| 2008/0223798 | A1 | 9/2008 | Paretta et al. |
| 2011/0139276 | A1 | 6/2011 | Kashmiran et al. |
| 2011/0256522 | A1 | 10/2011 | Ericson et al. |
| 2011/0290260 | A1 | 12/2011 | Tomes et al. |
| 2012/0077182 | A1 | 3/2012 | Bitensky et al. |
| 2012/0135391 | A1 | 5/2012 | Shaz et al. |
| 2013/0004937 | A1 | 1/2013 | Yoshida et al. |
| 2014/0065117 | A1 | 3/2014 | Gray |
| 2014/0212397 | A1 | 7/2014 | Gray et al. |
| 2014/0212400 | A1 | 7/2014 | Gray |

FOREIGN PATENT DOCUMENTS

| | | |
|---|---|---|
| WO | 2011103179 A1 | 8/2011 |
| WO | 2014039660 A1 | 3/2014 |

OTHER PUBLICATIONS

Burger, Patrick et al. An improved red blood cell additive solution maintains 2, 3-diphosphoglycerate and adenosine triphosphate levels by an enhancing effect on phosphofructokinase activity during cold storage. Transfusion, vol. 50, No. 11, (Nov. 29, 2010), pp. 2386-2392.

Button, L. et al. "Rejuvenation of red blood cells drawn in ADSOL to extend autologous red cell storage" (Abstract S54) Transfusion 26(6): 558, 1986.

Caridian BCT. COBE Spectra, Apheresis System. "Customized White Blood Cell Collections" 2009.

D'Alessandro, Angelo et al. Red blood cell strage: the story so far. Blood Transfus, (Mar. 29, 2010), pp. 82-88.

Dufour SP, et al; Erythrocyte-Dependent Regulation of Human Skeletal Muscle Blood Flow: Role of Varied Oxyhemoglobin and exercise on nitrite, S-nitrosohemoglobin, and ATP. Am J Physiol Heart Circ Physiol 299:H1936-H1946, (2010).

Haemonetics, ACP 215 Automated Cell Processor (2012).

Heaton, A. et al. "Use of ADSOL preservation solution for prolonged storage of low viscosity AS-1 red blood cells." BR. J. Haemo. 57:467-468, 1984.

Hess, J.R. An update on solutions for red cell storage. Vox Sanguinis, vol. 91, No. 1 (Jul. 1, 2006) pp. 13-19.

Hess, John R., Red cell storage. Journal of Proteomics, Elsevier, Amsterdam, NL., vol. 73, No. 3, (Jan. 3, 2010), pp. 368-373.

Hospira. "GemStar Pump Set-SL, Nonvented with 0.2 Micron Filter, 96 Inch." (2012).

Klein et al., "Red Blood Cell Transfusion in Clinical Practice" The Lancet, (Aug. 4, 2007), vol. 370, pp. 415-426.

Liu et al., "Microfluidic Chip Toward Cellular ATP and ATP-Conjugated Metabolic Analysis with Bioluminescence Detection" Analytical Chemistry, (Jan. 15, 2005), vol. 77, No. 2, pp. 573-578.

Lockwood et al. "Effects of Rejuvenation and Frozen Storage on 42-Day-Old AS-3 RBCs" Transfusion, (Nov. 2003) vol. 43, pp. 1527-1532.

Meyer, E. K. et al. "Rejuvenation capacity of red blood cells in additive solutions over long-term storage." Transfusion. Jul. 2011, vol. 51, No. 7: 1574-1579.

Rathburn, E.J. "Posttransfusion survival of red cells frozen for 8 weeks after 42-day liquid storage in AS-3." Transfusion 29(3):213-217, 1989.

Rejuvenation Handbook, A Comprehensive Guide to Red Cell Rejuvenation, enCyte™ Systems Inc., Brochure, (1977).

ReJuvesol® Red Blood Cell Processing Solution, enCyte™ Systems, Inc., Brochure (Mar. 1997).

Resnick, et al. A. J. Medical Sciences, 1994, Feb 307, Suppl. 1, SS66-9, Abstract Only.

Reynolds JD, et al. "The Transfusion Problem: Role of Aberrant S-Nitrosylation" Transfusion, 51:852-858, 2011.

Roback, John D., Vascular Effects of the Red Blood Cell Storage Lesion, Ameriacan Society of Hematology, Transfusion Medicine, Adverse Complications of Stored Blood, Hematology (2011).

Scott, K. L. et al. "Biopreservation of Red Blood Cells: Past, Present, and Future" Transfusion Medicine Reviews, Grune and Stratton, Orlando, FL (2005) vol. 19 No. 2: 127-142.

Song et al. "Multiplexed volumetric bar-chart chip for point-of-care diagnostics" Nat Commun. (2012) 3:1283.

Spiess et al. Pro: Autologous blood should be available for elective cardiac surgery. Journal of Cardio Thoracic and Vascular Anesthesia, Saunders, Philadelphia, PA, US, vol. 8, No. 2 (Apr. 1, 1994), pp. 231-237.

Stan et al., ROM. J. Intern. Med., 2009, vol. 47, No. 2, p. 173-177.

Valeri, C.R. "Simplification of the method for adding and removing glycerol during freezing preservation of human red blood cells with the high or low glycerol methods: Biochemical Modification prior to freezing." Trasfusion 15(3):195-218, 1975.

Valeri, C.R. et al. The survival, function and hemolysis of human RBCs stored at 4C in additive solution (AS-1, AS-3 or AS-5) for 42 days and then biochemically modified, frozen, thawed washed and stored at 4C in sodium chloride and glucose solution for 24 hours. Transfusion, American Association of Blood Banks, Bethesda, MD, US, vol. 40 (Nov. 1, 2000), pp. 1341-1345.

Valeri, C.R. et al. "A clinical experience with ADSOL preserved erythrocytes" Surg. Gyn. Obs. 166:33-46, 1988.

Valeri, C.R. et al., "Automation of the glycerolization of red blood cells with the high-separation bowl in the Haemonetics ACP 215 Instrument" Transfusion 2005, vol. 45, p. 1621-1627.

Valeri, C.R., Rejuvenation and Freezing of Outdated Stored Human Red Cells, New England Journal of Medicine 287:1.307-1313 (Dec. 28, 1972).

Van De Watering, L.M. G, et al. Beneficial Effects of Leukocyte Depletion of Transfused Blood on Postoperative Complications in

(56) References Cited

OTHER PUBLICATIONS

Patients Undergoing Cardiac Surgery: A Randomized Clinical Trial. Circulation, vol. 97, No. 6, (Feb. 17, 1998), pp. 562-568.

Veale, Margaret F. et al. Effect of additive solutions on red blood cell (RBC) membrane properties of stored RBCs prepared from whole blood held for 24 hours at room temperature. Transfusion Jan. 2011, vol. 51, Suppl 1, (Jan. 2011), pp. 255-335.

Yoshida, T., et al. The effects of additive solution pH and metabolic rejuvenation on anaerobic storage of red cells, Transfusion, vol. 48, No. 10, (Oct. 1, 2008), pp. 2096-2105.

Zimrin, A.B. et al. Current issues relating to the transfusion of stored red blood cells. Vox Sanguines, vol. 96, No. 2, (Feb. 1, 2009), pp. 93-103.

\* cited by examiner

FUNCTIONALLY-CLOSED, STERILE BLOOD PROCESSING SOLUTION SYSTEM AND METHOD

CROSS-REFERENCE TO RELATED APPLICATION

This application is a divisional of U.S. application Ser. No. 13/756,712, filed on Feb. 1, 2013, which is a continuation-in-part of U.S. application Ser. No. 13/756,116, filed on Jan. 31, 2013. The entire disclosures of each of the above applications are incorporated herein by reference.

The present disclosure relates to systems and processes for treating blood that has been drawn for transfusion.

Transfusion of blood is an important aspect of treating many disorders and injuries, such as treatment of accident victims and during surgical procedures. According to current American Red Cross statistics, about 5 million people receive blood transfusions yearly in the United States alone. A single accident victim can require as many as 100 pints of blood. Thus, the collection and distribution of blood and blood products is a vital part of the health care system. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during a medical procedure.

Donated blood is typically processed into components and then placed in storage until needed. Short term storage can be as long as six weeks, although blood or blood components can be frozen and stored for as long as ten years. During the processing of blood, materials may be added to the blood to preserve the vitality of its cellular components. It is important that such materials be added under sterile conditions.

Such materials include those that remedy the storage lesion that can occur in storage of blood. Unfortunately, the storage of red blood cells (RBCs) is associated altered energy production, oxygen delivery capacity, redox status, and structural/membrane integrity. For example, the concentration of adenine triphosphate (ATP) in stored RBCs decreases over time. Not only is ATP an energy source used by cells to catalyze numerous enzymatic reactions, ATP also signals endothelial cells to release nitric oxide (NO), which is a potent vasodilator. Additionally, the concentration of 2,3-diphosphoglycerate (2,3-DPG) within RBCs is significantly reduced after 14 days of storage, and is often undetectable after 21 days of storage. 2,3-DPG enhances the ability of RBCs to release oxygen by interacting with deoxygenated hemoglobin, decreasing the hemoglobin's affinity for oxygen, and thereby promoting the release of the remaining oxygen bound to the hemoglobin. Therefore, with diminished levels of ATP and 2,3-DPG, an RBC's ability to oxygenate tissue is severely impaired.

To rejuvenate RBCs before administration into a patient, blood is often incubated with an RBC enhancement composition. RBC enhancement compositions increase intracellular concentrations of 2,3-DPG and ATP, which improves the ability of RBCs to oxygenate tissues. RBC enhancement compositions typically comprise inosine, adenine, sodium pyruvate and sodium phosphate (dibasic and monobasic). A useful RBC enhancement composition is Rejuvesol® Red Blood Cell Processing Solution (Rejuvesol® Solution), which has been marketed by Cytosol Laboratories Inc. (now Citra Labs, LLC) since 1991.

Typically, such a blood rejuvenation product is added to the blood bag containing the RBC, by spiking the blood bag. Because spiking the blood bag is a non-sterile process, the blood is not stored for more than 24 hours after the blood bag is spiked. It is desirable to provide a functionally-closed, sterile system and process to deliver a blood rejuvenation product to blood (such as RBC) stored in a blood bag.

SUMMARY

In some aspects of the present disclosure a method of delivering a blood processing solution (e.g., an RBC enhancement composition) to blood present in a blood bag includes coupling a first end of a first tube to a vented spike and a second end of the first tube to a first input of a Y-shaped tube connector. An in-line microbiotic barrier filter is coupled to the first tube between the first and second ends of the first tube, wherein a flow path is created from the first end to the second end of the first tube that passes through the microbiotic barrier filter. A first end of a second tube is coupled to a transfer bag and a second end of the second tube is coupled to a second input of the Y-shaped tube connector. A first end of a third tube is coupled to an output of the Y-shaped tube connector. A second end of the third tube is sealed. Instructions are provided to seal a second end of a fourth tube that is coupled at a first end to the blood bag. Instructions are also provided to weld the third tube to the fourth tube using a sterile tubing welder.

In other aspects of the present disclosure a system for delivering a blood processing solution to blood present in a blood bag includes a functionally-closed, sterile Y-type tube set. The Y-type tube set includes a vented spike that is coupled to a first end of a first tube. A Y-shaped tube connector has a first and a second input and an output, wherein a second end of the first tube is coupled to the first input of the Y-shaped tube connector. An in-line microbiotic barrier filter is coupled to the first tube between the first and second ends of the first tube, wherein a flow path is created from the first end to the second end of the first tube that passes through the in-line microbiotic barrier filter. A transfer bag is coupled to a first end of a second tube, wherein a second end of the second tube is coupled to the second input of the Y-shaped tube connector. A third tube is coupled to the output of the Y-shaped tube connector, wherein a second end of the third tube is sealed. Indicia instructs a user to weld the third tube to a blood bag tube using a sterile tubing welder, wherein a functionally-closed, sterile flow path through which the blood processing solution can flow into the blood bag is maintained.

In still further aspects of the present disclosure a method of delivering a blood processing solution to blood present in a blood bag includes coupling a first end of a first tube to a vented spike and a second end of the first tube to a first input of a Y-shaped tube connector. An in-line microbiotic barrier filter is coupled to the first tube between the first and second ends of the first tube, wherein a flow path is created from the first end to the second end of the first tube that passes through the microbiotic barrier filter. A first end of a second tube is coupled to a transfer bag and a second end of the second tube is coupled to a second input of the Y-shaped tube connector. A first end of a third tube is coupled to an output of the Y-shaped tube connector. A second end of a third tube is sealed. A second end of a fourth tube is sealed that is coupled at a first end to the blood bag. The third tube is welded to the fourth tube using a sterile tubing welder, wherein a functionally-closed, sterile flow path through which the blood processing solution can flow into the blood bag is maintained.

In additional aspects of the present disclosure a functionally-closed, sterile Y-type tube set comprising a vented spike coupled to a first end of a first tube. A Y-shaped tube connector has a first and a second input and an output. A second end of the first tube is coupled to the first input of the Y-shaped tube connector. An in-line microbiotic barrier filter is coupled between the first and second ends of the first tube, wherein a flow path extends from the first end to the second end of the first tube that passes through the microbiotic barrier filter. A transfer bag is coupled to a first end of a second tube and a second end of the second tube is coupled to the second input of the Y-shaped tube connector. A third tube is coupled to the output of the Y-shaped tube connector, and a second end of the third tube is sealed.

In other aspects of the present disclosure method for delivering a blood processing solution to blood present in a blood bag comprises obtaining a functionally-closed sterile Y-type tube set comprising an input tubing member coupled to an output tubing member and providing a sterile flow path extending from a vented spike at a distal end of the input tubing member through an inline microbiotic filter and to a distal end of the output tubing member which is closed by a seal. The output tubing member is welded to a sealed input tubing member of the blood bag using a sterile tubing welder, wherein a functionally-closed, sterile flow path through which the blood processing solution can flow into the blood bag is maintained. The vented spike is inserted into a vial containing the blood processing solution to deliver the blood processing solution through the inline microbiotic filter and into the blood in the blood bag via the functionally-closed, sterile flow path.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

Example embodiments will now be described more fully with reference to the accompanying drawings. Numerous specific details are set forth in the exemplary embodiments described herein, such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Figure 1:
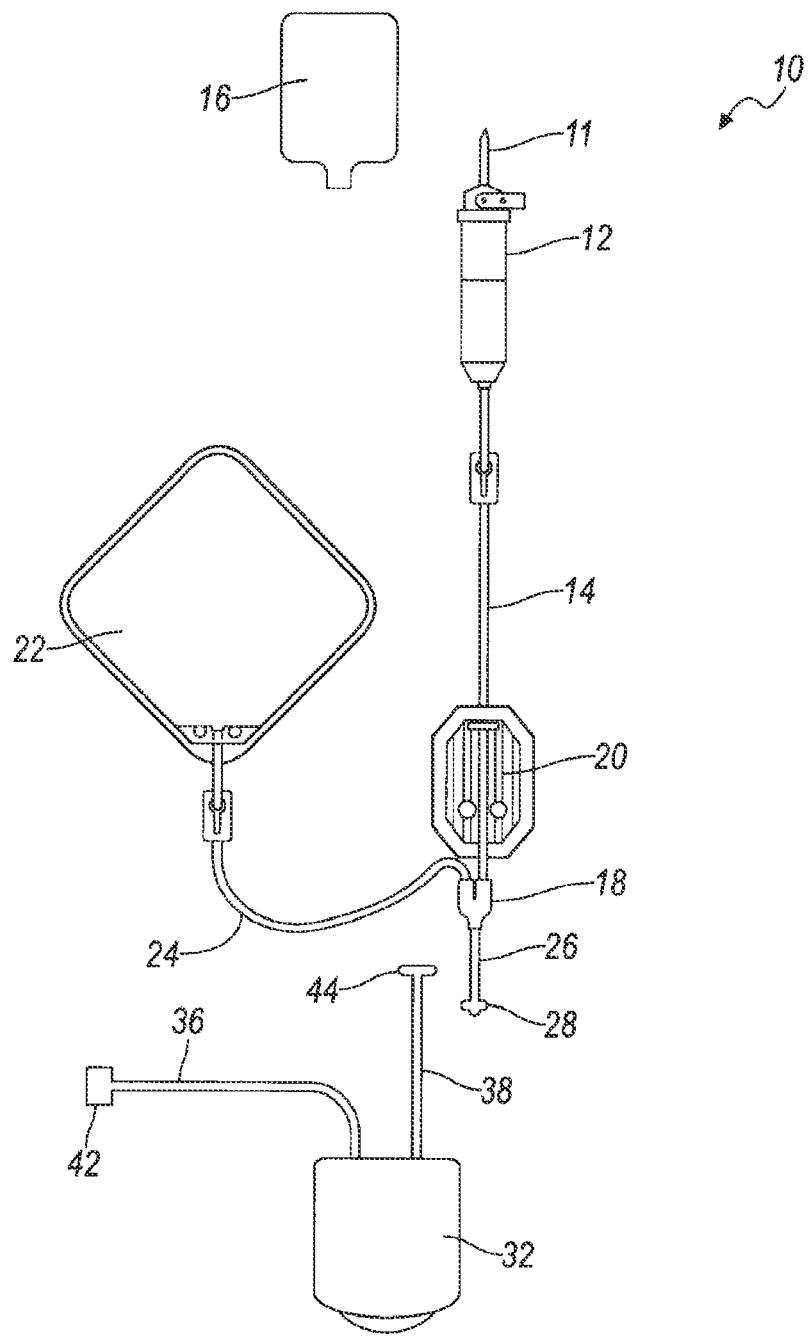
FIG. 1 is a plan view including a Y-type tube set that can be used in a process, and as a component of, a blood processing system.

FIG. 1 includes an illustration of a Y-type tube set 10 that can be used in a process, and as a component of, a blood processing system. (The term "blood" as used herein includes both whole blood and blood components, such as red blood cell (RBC) and plasma concentrates. Blood processing tube set 10 can include a vented spike 11 with drip chamber 12 coupled to the distal end of a first tube 14. Spike 11 can be inserted into a blood treatment vial or bottle 16 to complete a fluid communication channel between the interior of blood treatment vial 16 and first tube 14.

Blood treatment vial 16 can include an RBC processing composition, which can increase the levels of ATP and 2,3-DPG to original levels. In some embodiments, RBC processing compositions comprise one or more of the following components:

(a) about 2 to 30 g/L inosine (e.g., about 26.8 g/L inosine);
(b) about 5 to 15 g/L pyruvate (e.g., about 11 g/L sodium pyruvate);
(c) about 0.2 to 2 g/L adenine (e.g., about 0.7 g/L adenine); and
(d) about 10 to 30 g/L phosphate (e.g., a mixture of about 6.2 g/L monobasic, monohydrate; and about 14.6 g/L dibasic, heptahydrate).

An RBC processing composition useful in the methods of this technology has been commercialized by Citra Labs, LLC (formerly Cytosol Laboratories), Braintree, Mass., under the mark "Rejuvesol® Solution".

First tube 14 can be coupled at its second end to an input of a Y-shaped connector 18. An in-line microbiotic barrier filter 20 can be positioned in the first tube 14 flow path to filter the material flowing from the vented spike 11 through the first tube 14 to the input of Y-shaped connector 18. One exemplary in-line microbiotic barrier filter 20 is a flat 0.2 micron filter.

A transfer bag 22 can be coupled to a first end of a second tube 24. The second end of second tube 24 is coupled to the other input of Y-shaped connector 18. Transfer bag 22 can be initially empty and used to collect, for example, supernatant waste material. Additionally or alternatively, transfer bag 22 may initially include a processing agent, such as a wash solution.

Third tube 26 can be coupled to the output of Y-shaped connector 18 at its first end. A second end of third tube 26 is defined by a seal 28 sealing the fluid channel of third tube 26. For example, seal 28 can be welded closed using a radio frequency (RF) tube sealer (not shown). Given that no potential entry point of Y-type tube set 10 is initially unsealed or unprotected by a microbiotic barrier filter, this Y-type tube set 10 is functionally-closed. In other words, Y-type tube set 10 provides a functionally-closed, sterile fluid pathway (via third tube 26) for blood processing solution from bottle 16 to be delivered into blood bag 32.

Figure 2:
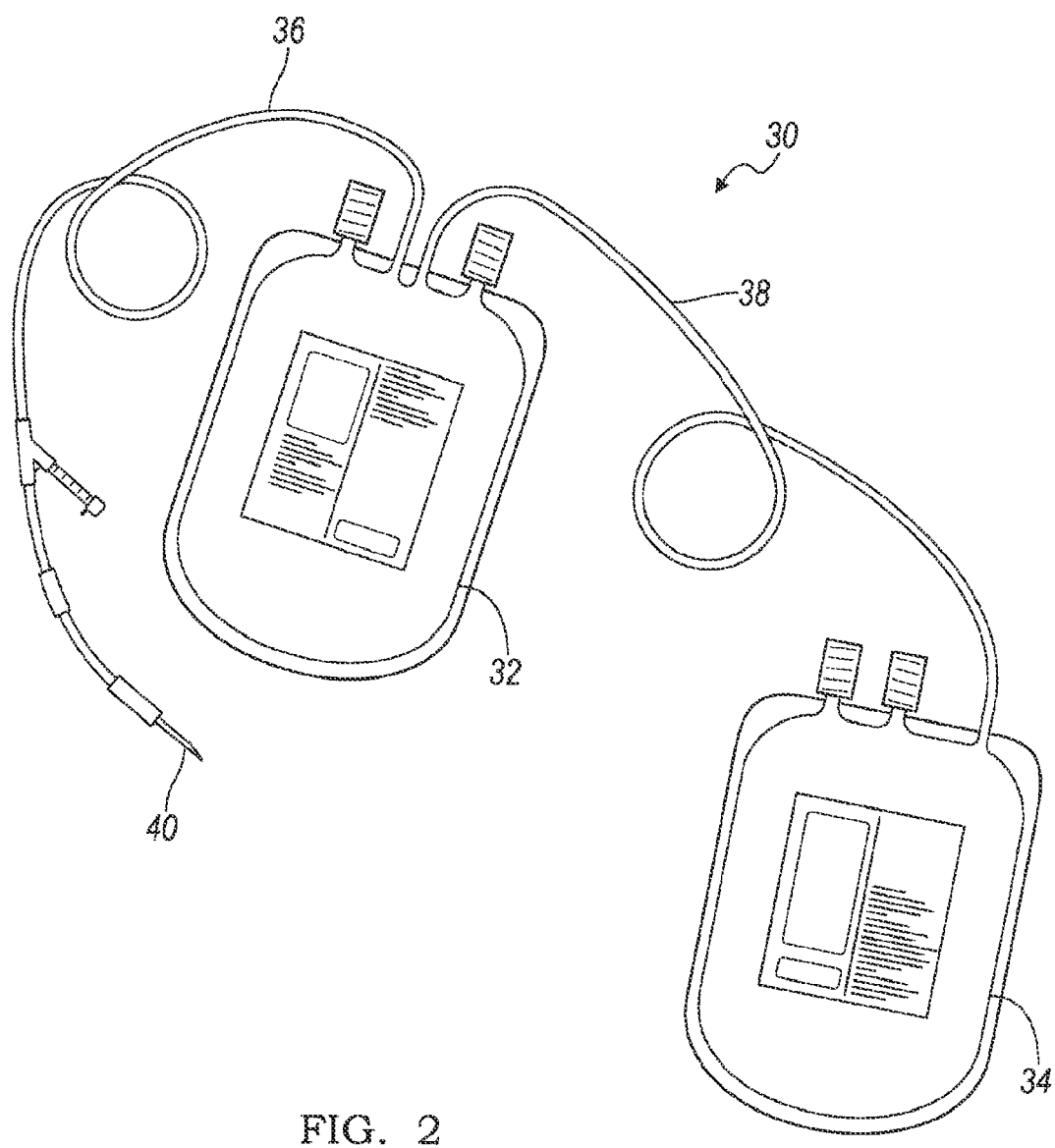
FIG. 2 is a plan view of a blood collection bag set which can be used in conjunction with the Y-type tube set of FIG. 1.

FIG. 2 is an illustration of blood collection bag set 30 which can be a component of a blood collection and processing system. Blood collection bag set 30 can include blood bag 32 and at least one transfer bag 34. Such blood bags 32 typically include at least two integral conduits or tubes 36 and 38. One of the integral tubes 36 can initially have a needle 40 at its distal end and is used to draw blood from a blood donor into blood bag 32. Second integral tube or conduit 38 can initially be integrally coupled to transfer bag 34, which can be initially empty or can contain a processing agent.

As illustrated in FIG. 1, sometime after blood is collected into blood bag 32, tubes 36 and 38 can be sealed. Sealing of tubes 36 and 38 can be accomplished by welding tubes 36 and 38 closed using, for example, an RF tube sealer. Thus, the distal portion of tube 36 including needle 40 that is downstream of the end created by seal 42 can be removed. Similarly, the distal portion of tube 38 including transfer bag 34 that is downstream of the end created by seal 44 can be removed. Though not always the case, the blood remaining in blood bag 32 at the point the transfer bag(s) 34 are removed can be a RBC.

When it is desired to maintain the functionally-closed nature of the fluid pathway delivering blood processing solution via Y-type tube set 10 into blood bag 32, third tube 26 can be coupled to tube 38 of blood bag 32 using a sterile tubing welder 45.

Figure 3A:
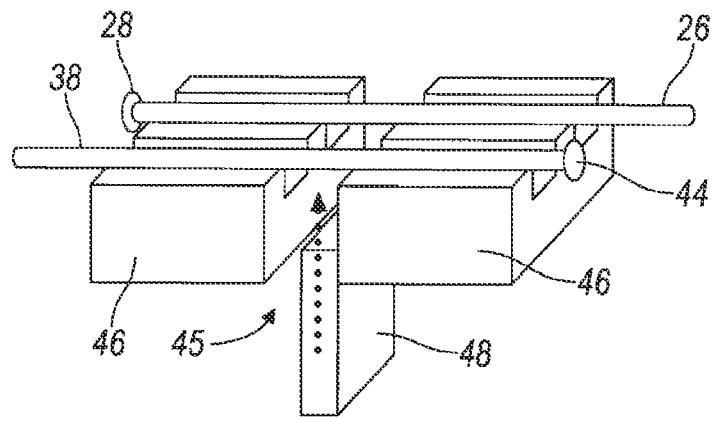
FIGS. 3A-3C are diagrammatic illustrations of sterile tube welder operations that can be used in conjunction with the Y-type tube set of FIG. 1.

Referring to FIG. 3A, such sterile tubing welders 45 can operate using clamps 46 to position third tube 26 of Y-type tube set 10 and tube 38 of blood bag 32 adjacent each other with the seals at opposing ends as illustrated in FIG. 3A. After clamping tubes 26 and 38 in place, a blade 48 can be heated to 400 degrees and then moved upwardly to simultaneously sever tubes 26 and 38.

Figure 3B:
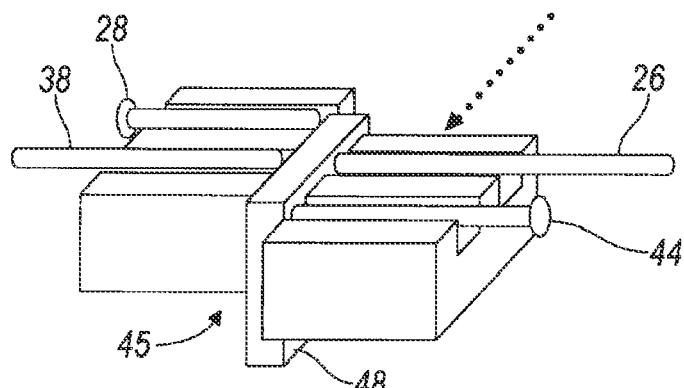
Figure 3C:
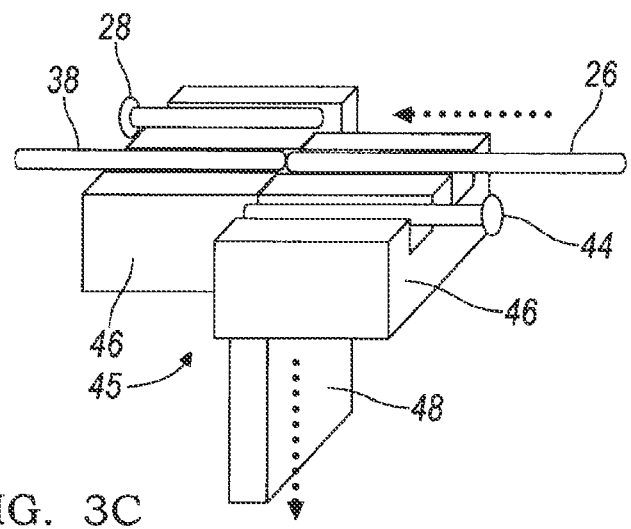

Referring to FIG. 3B, clamps 46 can then translate relative to each other to align the cut end of tubes 26 and 38 together. As illustrated in FIG. 3C, heated blade 48 can be withdrawn and the heated, cut ends of tubes 26 and 38 can be positioned against each other; thereby welding tubes 26 and 38 together in a sterile process. Accordingly, the created fluid pathway, including third tube 26 and tube 38 of blood bag 32 can be joined together while maintaining the sterile, functionally-closed, state of this pathway. Notably, this can enable a blood processing solution to be delivered from bottle 16 to blood bag 32 without spiking the blood bag 32, for example, with a needle. An exemplary tubing welder 45 that can be used is the Terumo TSCD®-II sterile tubing welder.

Figure 4:
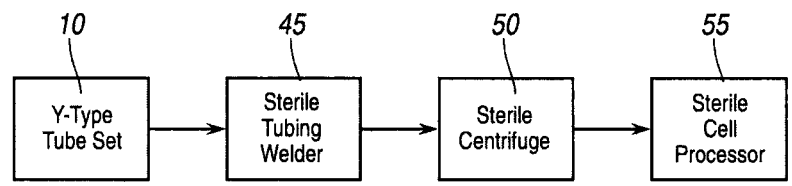
FIG. 4 is a diagrammatic view of various functionally-closed, sterile components that can be used in a process, and as components of, a blood processing system.

Because the blood processing solution can be delivered from bottle 16 to blood bag 32 via a functionally-closed, sterile fluid pathway, the blood can be stored for more than 24 hours after such delivery. Referring to FIG. 4, additional post-processing devices can be used to further process the blood while maintaining the blood in a functionally-closed, sterile environment.

With continuing reference to FIG. 4, the blood of blood bag 32 can be processed using a functionally-closed, sterile centrifuge 50. This can be done, for example, prior to delivering the blood processing solution to the blood bag 32 to remove components of whole blood and leave RBC in blood bag 32. One exemplary functionally-closed, sterile centrifuge 50 is the COBE Spectra Apheresis System.

Similarly, the blood of blood bag 32 can be washed using a functionally-closed, sterile cell processor 55. Such a cell processor 55 can be used to remove a blood processing solution from the blood in blood bag 32, including, for example, deglycerolization. One exemplary functionally-closed, sterile cell processor 55 is the Haemonetics® ACP®215 Automated Cell Processor.

Figure 5:
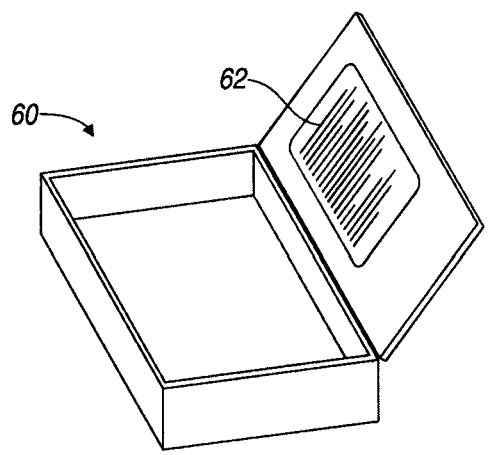
FIG. 5 is a perspective view of a package that can be used for the Y-type tube set of FIG. 1, including indicia.

Referring to FIG. 5, a package 60 for Y-type tube set 10 can comprise indicia 62. For example, indicia 62 can be printed on package 60 or a package label. As another example, package 60 can include a printed package insert or pamphlet providing indicia 62. Indicia 62 can include instructions to seal a second end of a fourth tube 38 that is coupled at a first end to blood bag 32. Indicia 62 can also include instructions to weld third tube 26 to fourth tube 38 using a sterile tubing welder 45. Indicia 62 can further include information indicating that the blood can be stored for use for more than 24 hours after delivering the blood processing solution into the blood bag 32.

Alternatively, indicia 62 including instructions and information can be provided separate from any package 60. For example, such instructions and information can be provided via a website or advertising materials, including brochures and pamphlets. Such instructions and information can also be provided indirectly. For example, package 60, advertising, or an associated website might correlate a Y-type tube set 10 to a competitive product that includes such instructions and information.

Non-Limiting Discussion of Terminology

The foregoing description of various embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. In particular, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested. Equivalent changes, modifications and variations of some embodiments, materials, compositions and methods can be made within the scope of the present technology, with substantially similar results.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition or method.

As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. Similarly, the terms "can" and "may" and their variants are intended to be non-limiting, such that recitation that an embodiment can or may comprise certain elements or features does not exclude other embodiments of the present technology that do not contain those elements or features. The method steps, processes, and operations described herein are not to be construed as necessarily requiring their performance in the particular order discussed or illustrated, unless specifically identified as an order of performance. It is also to be understood that additional or alternative steps may be employed.

In particular, although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A functionally-closed, sterile Y-type tube set comprising:
    a vented spike coupled to a first end of a first tube;
    a Y-shaped tube connector having a first and a second input and an output, wherein a second end of the first tube is coupled to the first input of the Y-shaped tube connector;
    an in-line microbiotic barrier filter coupled between the first and second ends of the first tube, wherein a flow path extends from the first end to the second end of the first tube that passes through the microbiotic barrier filter;
    a transfer bag coupled to a first end of a second tube, wherein a second end of the second tube is coupled to the second input of the Y-shaped tube connector; and
    a third tube coupled to the output of the Y-shaped tube connector, wherein a second end of the third tube is sealed.

2. The functionally-closed, sterile Y-type tube set of claim 1, wherein the inline microbiotic filter is a 0.2 micron IV filter.

3. The Y-type tube set of claim 1, wherein the transfer bag is empty.

4. The Y-type tube set of claim 1, wherein the transfer bag includes a wash solution.

5. A method for delivering a blood processing solution to a blood component present in a blood bag, the method comprising:
    obtaining a functionally-closed sterile tube set comprising i) Y-type tube connector, (ii) a first tube providing a flow path extending from a vented spike at a first end of the first tube through an inline microbiotic filter to a second end of the first tube, the second end coupled to a first input of the Y-type tube connector, (iii) a transfer bag coupled to a second input of the Y-type tube connector, and (iv) a sealed output tube coupled to an output of the Y-type tube connector;
    welding the sealed output tube to a sealed input tubing of a blood bag using a sterile tubing welder, wherein a functionally-closed, sterile flow path is maintained through which a blood processing solution can flow into the blood bag; and
    inserting the vented spike into avid containing the blood processing solution to deliver the blood processing solution through the inline microbiotic filter and into a blood component in the blood bag.

6. The method of claim 5, further comprising storing the treated blood component greater than 24 hours for use thereafter.

7. The method of claim 5, wherein the in-line microbiotic barrier filter is a 0.2 micron IV filter.

8. The method of claim 5, further comprising increasing the intracellular content of ATP and 2,3-DPG of the blood component as a result of delivering the blood processing solution to the blood component.

9. The method of claim 5, wherein blood component comprises a red blood cell concentrate, the method further comprising increasing the intracellular content of adenosine triphosphate and 2,3-diphosphoglycerate of the red blood cell concentrate as a result of delivering the blood processing solution to the red blood cell concentrate.

10. The method of claim 5, further comprising processing the blood and blood processing solution together using a functionally-closed, sterile cell processor.

11. The method of claim 5, further comprising processing the blood and blood processing solution together using a functionally-closed, sterile centrifuge.

12. A blood processing system, comprising:
a Y-shaped tube connector having a first input, a second input, and an output;
a first tube comprising an in-line filter, the first tube coupled to the first input;
a transfer bag coupled to the second input; and
an output tube coupled to the output of the Y-shaped tube connector, the output tube having a sealed end;
a vented spike configured to be coupled to the first tube; and
a container comprising a blood processing composition, the container configured to be pierced by the vented spike.

13. The blood processing system of claim 12, wherein the transfer bag is empty.

14. The blood processing system of claim 12, wherein the transfer bag includes a wash solution configured to wash a blood product.

15. The blood processing system of claim 12, wherein the blood processing composition comprises inosine, pyruvate, adenine, and a phosphate mixture.

16. The blood processing system of claim 15, wherein the blood processing composition comprises between about 2 to 30 g/L inosine, between about 5 to 15 g/L pyruvate, between about 0.2 to 2 g/L adenine, and between about 10 to 30 g/L phosphate.

17. The blood processing system of claim 15, wherein the blood processing system is packaged in a single container.

18. The blood processing system of claim 17, wherein the container includes instructions for use of the blood processing system.

19. The blood processing system of claim 12, wherein the in-line filter is a 0.2 micron filter.

20. The blood processing system of claim 12, wherein the transfer bag is coupled to second input through a tube.

* * * * *

UNITED STATES PATENT AND TRADEMARK OFFICE
CERTIFICATE OF CORRECTION

PATENT NO. : 9,550,015 B2
APPLICATION NO. : 14/634264
DATED : January 24, 2017
INVENTOR(S) : Alan Gray Page 1 of 1

It is certified that error appears in the above-identified patent and that said Letters Patent is hereby corrected as shown below:

On the Title Page

In item (73), in "Assignee", in Column 1, Line 1, delete "Biologies," and insert --Biologics,-- therefor On page 2, in Column 2, under "Other Publications", Line 3, delete "strage:" and insert --storage:-- therefor On page 2, in Column 2, under "Other Publications", Line 42, delete "Ameriacan" and insert --American-- therefor In the Claims In Column 8, Line 48, in Claim 5, delete "1)" and insert --(i)-- therefor In Column 8, Line 61, in Claim 5, delete "avid" and insert --a vial-- therefor In Column 9, Line 7, in Claim 9, after "wherein", insert --the--

In Column 10, Line 26, in Claim 20, after "to", insert --the--

Signed and Sealed this
Twelfth Day of June, 2018

Andrei Iancu
*Director of the United States Patent and Trademark Office*